United States Patent [19]

Murib et al.

[11] 4,338,290

[45] Jul. 6, 1982

[54] HYDROLYSIS OF HALOHYDRIN OR DIHALIDE WITH HI CATALYST

[75] Inventors: Jawad H. Murib; John M. Inskeep, both of Cincinnati, Ohio

[73] Assignee: National Distillers & Chemical Corp., New York, N.Y.

[21] Appl. No.: 159,979

[22] Filed: Jun. 16, 1980

[51] Int. Cl.³ .................... C07C 31/20; C01B 7/01
[52] U.S. Cl. .................... 423/481; 423/483; 568/811; 568/821; 568/833; 568/838; 568/839; 568/859
[58] Field of Search ............ 568/859, 894, 811, 821, 568/833, 838, 839; 423/481, 483

[56] References Cited

U.S. PATENT DOCUMENTS

| | | | |
|---|---|---|---|
| 2,056,976 | 10/1936 | Mnookin | 568/859 |
| 2,124,426 | 7/1938 | McKee | 568/859 |
| 2,130,891 | 9/1938 | Mnookin | 568/859 |
| 2,806,888 | 9/1957 | Davis | 568/859 |
| 2,819,319 | 1/1958 | Barnes | 568/894 |
| 3,005,845 | 10/1961 | Bain | 568/859 |
| 3,018,308 | 1/1962 | Levine et al. | 568/894 |
| 3,691,218 | 9/1972 | Heckert | 568/859 |
| 3,931,238 | 1/1976 | Starks | 568/894 |
| 3,992,432 | 11/1976 | Napier et al. | 568/852 |

FOREIGN PATENT DOCUMENTS

| | | | |
|---|---|---|---|
| 361042 | 8/1920 | Fed. Rep. of Germany | 568/894 |
| 2633228 | 2/1977 | Fed. Rep. of Germany | 568/859 |

OTHER PUBLICATIONS

Groggins, "Unit Processes in Organic Synthesis", 4th ed. (1952), p. 664.
Herriott et al., "Tetrahydron Letters", No. 44 (1972), pp. 4521–4524.
Duynstee et al., "Tetrahydron", 1965, vol. 21, pp. 2401–2412.

*Primary Examiner*—Joseph E. Evans
*Attorney, Agent, or Firm*—Kenneth D. Tremain

[57] ABSTRACT

Glycols are readily and conveniently prepared by hydrolysis of halohydrins and/or dihaloalkanes in the presence of a catalytically effective amount of a strong acid.

16 Claims, No Drawings

HYDROLYSIS OF HALOHYDRIN OR DIHALIDE WITH HI CATALYST

This application relates to subject matter disclosed in commonly assigned copending U.S. patent application Ser. No. 159,978 and Ser. No. 159,977, filed on even date herewith, each entitled "Process for the Preparation of Tetrahydrofuran".

BACKGROUND OF THE INVENTION

1. Field of the Invention

This invention relates to the field of glycols and more particularly, to processes for obtaining glycols from the hydrolysis of halohydrins and dihaloalkanes.

2. Description of the Prior Art

Numerous processes are known for obtaining glycols from the hydrolysis of halohydrins and dihaloalkanes (viz., U.S. Pat. Nos. 1,442,386; 1,594,608; 1,626,398; 1,695,250; 1,709,605; 1,895,517; 1,996,193; 2,047,811; 2,181,297; and, 2,838,574). These processes employ alkali metal hydroxides and/or alkali metal carbonates in the hydrolysis media in order to provide a receptor for the haloacid which is generated by the reaction. The overall reaction (illustrated for the production of 1,3-propanediol from propylene chlorohydrin using aqueous sodium hydroxide) is as follows:

$$ClCH_2CH_2CH_2OH + NaOH \rightarrow HOCH_2CH_2CH_2OH + NaCl$$

In this reaction, one mole of alkali metal hydroxide must be used for each mole of halohydrin hydrolyzed to glycol and when dihalide is employed as the glycol precursor, two moles of alkali metal hydroxide must be employed. Such a substantial requirement of alkali metal hydroxide (or alkali metal carbonate) places these synthetic procedures for obtaining glycols at a considerable competitive disadvantage compared to other synthetic procedures for obtaining glycols. Moreover, since the haloacid produced by the prior art processes is completely neutralized, a valuable reagent for preparing additional quantities of halohydrin (viz., U.S. Pat. No. 3,277,187) is lost.

Accordingly, there has heretofore existed a need for an economically efficient process for hydrolyzing halohydrins and dihaloalkanes to the corresponding glycols which does not require the consumption of alkali metal hydroxides and/or alkali metal carbonates and which permits recovery of the haloacid by-product.

SUMMARY OF THE INVENTION

It has surprisingly been found that strong acids will effectively catalyze the hydrolysis of halohydrins and/or dihaloalkanes to provide the corresponding glycols. In addition to avoiding the consumption of large quantities of alkali metal hydroxide/carbonate, the haloacid by-product of this process can be recycled to form additional halohydrin, e.g., by the process described in U.S. Pat. No. 3,277,187 which is incorporated by reference herein.

In accordance with the process of this invention, a halohydrin and/or dihalide of the general formula $$X—R—Y$$

in which X is a halogen atom, Y is a halogen atom or a hydroxyl group and R is an unbranched alkylene or cycloalkylene group of from 2 to about 12 carbon atoms or a branched alkylene or cycloalkylene group of from 2 to about 12 carbon atoms in the main chain and containing one or more alkyl, cycloalkyl, aryl, alkaryl or aralkyl groups of a total of from 1 to about 12 carbon atoms, is reacted with water in the presence of a catalytically effective amount of a strong acid to provide a glycol of the general formula $$HO—R—OH$$

in which R has the same meaning given above, and haloacid.

DESCRIPTION OF THE PREFERRED EMBODIMENTS

Halohydrins and dihaloalkanes which can be used for the preparation of glycols in accordance with the invention herein are, preferably, those compounds in which the alkylene group contains from about 2 to about 6 carbon atoms and the halogen substituent is chlorine and/or fluorine. Especially preferred are those compounds in which the alkylene group contains from about 2 to about 4 carbon atoms, e.g., 2-chloroethanol-1, 3-chloropropanol-1, 2-chloropropanol-1, 1-chlorobutanol-2, 1,2-dichloroethane, 1,3 dichloropropane, 1,4 dichlorobutane, and the like.

It is desirable to carry out the hydrolysis reaction in the presence of a phase transfer agent or an emulsifying agent to facilitate the hydrolysis and shorten the reaction time. Phase transfer agents useful in the hydrolysis include alkali metal tetraaryl boron, e.g., sodium tetraphenyl boron; quaternary ammonium or phosphonium salts in which the anion is halide, hydroxide, sulfate, bisulfate, phosphate; and the like. Suitable emulsifying agents include fatty acid salts of Group 1A metals, and the like.

Optionally, the hydrolysis reaction can be carried out in any inert solvent which will dissolve the alkylene halohydrin or dihalide and which is miscible with water. Such solvents include cyclic ethers such as tetrahydrofuran, dioxane and tetrahydropyran; ethers such as methyl ethers of ethylene glycols; ketones such as acetone; lactones of hydroxy organic acids such as butyrolactone; organic acids; monoalcohols; glycols such as ethylene glycol and 1,3-propylenediol; and the like. Where it is desirable to use a mutual solvent system, it is generally preferred to employ a glycol which is the same as the one sought as the solvent for the sake of convenience and simplicity.

The reaction conditions are not overly critical in that wide ranges of temperature and pressures are operable. The practical limitations of production equipment will dictate to a great extent the selection of temperatures and pressure at which the reaction is to be effected. Thus, using available production systems, the selected temperature should be at least about 20° C. and can range up to about 350° C. and even higher. For most purposes, the preferred operating temperature ranges from about 75° C. to about 250° C. The pressure can range from somewhat below atmospheric to as high as 160 atmospheres. Most desirably, the pressure should be in the range of from about atmospheric to about 50 atmospheres, particularly when employing the aforesaid preferred temperature range. In the case of the conversion of 1,4-dihalobutane or 4-halobutanol-1 to 1,4-butanediol by the process herein, it has been observed that, if the product diol is permitted to remain in the reaction medium for relatively lengthy periods, e.g., five hours or more, yields will be reduced (cf. U.S. patent application Ser. No. 159,978 referred to supra). Accordingly, in the case of 1,4-butanediol at least, the diol product should be recovered either as it is produced or as the conversion reaction nears or reaches completion as determined, for example, by chromatographic analysis.

The catalyst for the hydrolysis reaction herein is a strong acid. The term "strong acid" as used herein embraces organic and inorganic acids which are highly dissociated in water. Such acids are well known in the art and include hydriodic acid, sulfuric acid, sulfonic acid, especially the arylsulfonic acids, phosphoric acid, phosphonic acid, especially the arylphosphonic acids, and the like. Strong inorganic acids such as hydriodic acid, sulfuric acid and phosphoric acid are particularly advantageous for use as catalysts herein. The amount of strong acid catalyst employed does not seem to be critical and can vary considerably. At least a catalytically effective amount of catalyst should be used, of course. In general, an amount of catalyst which is effective to provide a reasonable reaction rate is sufficient. In practice, an amount of strong acid in the range of from about 0.001 to about 0.1 moles, and preferably from about 0.002 to about 0.025 moles per mole of 1,4-dihalobutane, provides good results.

Recovery of the product glycol can be accomplished by any of the known and routine techniques, e.g., distillation.

Examples 1 to 9 further illustrate the invention.

EXAMPLE 1

The following were charged to a reactor:

| | | |
|---|---|---|
| 4.52 | g | 3-chloropropanol-1 (89.7%) |
| 0.2 | ml | hydriodic acid (57% by weight) |
| 20 | g | water |

The above mixture was placed in a 150 ml Fisher Porter glass tube equipped with a magnetic stirrer and sealed. The vessel was heated for twelve hours in an oil bath at 90° C. with stirring. After the reaction mixture had cooled, chromatographic analysis and mass spectral analysis indicated the presence of 1,3-propanediol. The conversion amounted to 50.4 mole percent.

EXAMPLE 2

The following were charged to a reactor:

| | | |
|---|---|---|
| 2.26 | g | 3-chloropropanol-1 |
| 0.1 | ml | hydriodic acid (57% by weight) |
| 18.0 | g | water |

The above mixture was placed in a 150 ml Fisher Porter glass tube equipped with a magnetic stirrer and sealed. The vessel was heated overnight in an oil bath at 100° C. with stirring. After the reaction mixture had cooled, chromatographic analysis and mass spectral analysis indicated the presence of 1,3-propanediol. The conversion amounted to 72 mole percent.

EXAMPLE 3

The following were charged to a reactor:

| | | |
|---|---|---|
| 3.39 | g | 3-chloropropanol-1 (89.7%) |
| 0.15 | ml | hydriodic acid (57% by weight) |
| 18.0 | g | water |

The above mixture was placed in a 150 ml Fisher Porter glass tube equipped with a magnetic stirrer and sealed. The vessel was heated for twelve hours in an oil bath at 117° C. with stirring. After the reaction mixture had cooled, chromatographic analysis and mass spectral analysis indicated the presence of 1,3-propanediol. The conversion amounted to 71.9 mole percent.

EXAMPLE 4

The following were charged to a three-neck round bottom flask provided with a high speed mixer, a nitrogen inlet and temperature control:

| | | |
|---|---|---|
| 3.0 | ml | 1,4-dichlorobutane |
| 24.0 | ml | water |
| .15 | ml | sodium lauryl sulfate |
| .30 | | hydriodic acid (57% by weight) |

The reaction medium was blanketed with nitrogen and heated to from 100° C.–105° C. with constant mixing. After a reaction period of four hours, analysis of the reaction medium indicated the presence of 1,4-butanediol.

EXAMPLE 5

A mixture of 11.9 g 1,4-dichlorobutane (82% purity), 30 g of water and 1 ml of concentrated sulfuric acid as catalyst was heated in a shaking Hastelloy reactor (2.5 cm inside diameter×13.8 cm deep) at 170° C. for 2 hours. Upon cooling, the reaction mixture was found to contain 1,4-butanediol (by chromatography).

EXAMPLE 6

Example 5 is repeated except 1 ml of 85% $H_3PO_4$ was used as catalyst instead of sulfuric acid. The reaction mixture contained 1,4-butanediol.

EXAMPLE 7

A mixture of 11.3 g 1,4-dichlorobutane (82%), 20 g water, 0.25 ml aqueous hydriodic acid (57%) as catalyst and 0.2 g tetradecyltrimethylammonium bromide was placed in a 125 ml 3-neck round bottom flask equipped with a high speed stirrer, condenser and a serum cap for sample withdrawal. The Reaction medium was heated at reflux for 0.5 hour. The reaction mixture contained 1,4-butanediol.

EXAMPLE 8

Example 7 is repeated except 0.5 g hexadecyltributylphosphonium bromide was used in place of the tetradecyltrimethylammonium bromide as the transfer agent. The reaction mixture contained 1,4-butanediol.

EXAMPLE 9

The following are charged to a three-neck round bottom flask provided with a high speed stirrer, a nitrogen inlet and temperature control

| | | |
|---|---|---|
| 3.0 | ml | 1,4-dichlorobutane |
| 24.0 | ml | water |
| 0.15 | ml | Hydriodic acid (57% by weight) |

-continued

| 0.2 | g | sodium tetraphenyl boron (NaBPh4) |

The reaction medium was blanketed with nitrogen and heated at 105° C. for two hours. The reaction mixture contained 1,4-butanediol.

What is claimed is:

1. A process for preparing glycols which comprises reacting a compound of the general formula

X—R—Y in which X is a halogen atom, Y is a halogen atom or a hydroxyl group and R is an unbranched alkylene or cycloalkylene group of from 2 to about 12 carbon atoms or a branched alkylene or cycloalkylene group of from 2 to about 12 carbon atoms in the main chain and containing one or more alkyl, cycloalkyl, aryl, alkaryl or aralkyl groups of a total of from 1 to about 12 carbon atoms, with water in the presence of a catalytically effective amount of a catalyst composition consisting of hydriodic acid to provide a glycol of the general formula

HO—R—OH in which R has the same meaning given above, and haloacid.

2. The process of claim 1 wherein the compound of the general formula X—R—Y is a halohydrin.

3. The process of claim 2 wherein the halohydrin is propylene chlorohydrin.

4. The process of claim 1 wherein the compound of the general formula X—R—Y is a dihaloalkane.

5. The process of claim 4 wherein the dihaloalkane is dichloropropane.

6. The process of claim 1 wherein water is present in stoichiometric excess.

7. The process of claim 1 wherein the temperature of the reaction is from about 20° C. to about 350° C.

8. The process of claim 7 wherein the temperature of the reaction is from about 75° C. to about 250° C.

9. The process of claim 1 wherein the pressure of the reaction is from below atmospheric to about 160 atmospheres.

10. The process of claim 9 wherein the pressure of the reaction is from atmospheric to about 50 atmospheres.

11. The process of claim 1 wherein from about 0.001 to about 0.1 moles of hydriodic acid per mole of X—R—Y compound are employed.

12. The process of claim 3 or 5 wherein a phase transfer agent or emulsifying agent is employed.

13. The process of claim 12 wherein the phase transfer agent is a member selected from the group consisting of alkali metal tetraaryl boron, quaternary ammonium bromide and quaternary phosphonium bromide.

14. The process of claim 13 wherein the phase transfer agent is sodium tetraphenyl boron.

15. The process of claim 13 wherein the phase transfer agent is tetradecyltrimethylammonium bromide.

16. The process of claim 13 wherein the phase transfer agent is hexadecyltributylphosphonium bromide.

* * * * *